(12) United States Patent
Katsevich

(10) Patent No.: US 6,898,264 B2
(45) Date of Patent: May 24, 2005

(54) METHOD OF RECONSTRUCTING IMAGES FOR SPIRAL AND NON-SPIRAL COMPUTER TOMOGRAPHY

(75) Inventor: Alexander Katsevich, Oviedo, FL (US)

(73) Assignee: Research Foundation of the University of Central Florida, Orlando, FL (US)

(*) Notice: Subject to any disclaimer, the term of this patent is extended or adjusted under 35 U.S.C. 154(b) by 73 days.

(21) Appl. No.: 10/858,008

(22) Filed: Jun. 1, 2004

(65) Prior Publication Data
US 2004/0223581 A1 Nov. 11, 2004

Related U.S. Application Data

(60) Division of application No. 10/389,090, filed on Mar. 14, 2003, now Pat. No. 6,771,733, and a continuation-in-part of application No. 10/143,160, filed on May 10, 2002, now Pat. No. 6,574,299.
(60) Provisional application No. 60/379,547, filed on May 10, 2002, and provisional application No. 60/312,827, filed on Aug. 16, 2001.

(51) Int. Cl.$^7$ ................................................ A61B 6/03
(52) U.S. Cl. ......................................... 378/4; 378/901
(58) Field of Search ........................ 378/4, 8, 15, 19, 378/901

(56) References Cited

U.S. PATENT DOCUMENTS

| | | | |
|---|---|---|---|
| 5,663,995 A | 9/1997 | Hu | 378/15 |
| 5,706,325 A | 1/1998 | Hu | 378/4 |
| 5,784,481 A | 7/1998 | Hu | 382/131 |
| 5,881,123 A | 3/1999 | Tam | 378/4 |
| 5,926,521 A | 7/1999 | Tam | 378/4 |
| 5,960,055 A | 9/1999 | Samarasekera | 378/4 |
| 5,995,580 A | 11/1999 | Schaller | 378/15 |
| 6,009,142 A | 12/1999 | Sauer | 378/15 |

(Continued)

OTHER PUBLICATIONS

Danielsson, et al., *Towards Exact 3D–Recpmstriction for Helical Cone–Beam Scanning of Long Objects. A New Detector Arrangement and a New Completeness Condition,* Internation meeting on fully three dimensional image reconstruction in radiology, nuclean medicine. Jun. 25–28, Pittsburgh, Pa. p. 141–144.

(Continued)

Primary Examiner—David V Bruce
(74) Attorney, Agent, or Firm—Brian S. Steinberger; Law Offices of Brian S. Steinberger, P.A.

(57) ABSTRACT

General scheme processes and systems for constructing algorithms for reconstructing images of objects that have been scanned in a spiral or non-spiral fashions with detectors. Application of the scheme requires finding of a weight function, which would lead to the required reconstruction algorithm. This general scheme can use a C-arm scan with the closed x-ray source trajectory and gives a new, theoretically exact and efficient (i.e., with the convolution-based FBP structure) reconstruction algorithm. The invention can also utilize the algorithms disclosed in an earlier application U.S. patent application Ser. No. 10/143,160 filed May 10, 2002, entitled: Exact Filtered Back Projection (FBP) Algorithm For Spiral Computer Tomography, which claims the benefit of U.S. Provisional Application No. 60/312,827 filed Aug. 16, 2001, also fit into the general scheme.

2 Claims, 7 Drawing Sheets

U.S. PATENT DOCUMENTS

| | | | | |
|---|---|---|---|---|
| 6,014,419 | A | | 1/2000 | Hu .............................. 378/4 |
| 6,072,851 | A | | 6/2000 | Sivers ......................... 378/15 |
| 6,130,930 | A | | 10/2000 | Tam ............................. 378/4 |
| 6,173,032 | B1 | | 1/2001 | Besson ........................ 378/19 |
| 6,198,789 | B1 | | 3/2001 | Dafni ........................... 378/8 |
| 6,215,841 | B1 | | 4/2001 | Hsieh ........................... 378/8 |
| 6,233,303 | B1 | | 5/2001 | Tam ............................. 378/4 |
| 6,266,388 | B1 | | 7/2001 | Hsieh ........................... 378/8 |
| 6,324,241 | B1 | * | 11/2001 | Besson .......................... 378/4 |
| 6,459,754 | B1 | | 10/2002 | Besson .......................... 378/4 |
| 6,574,297 | B2 | * | 6/2003 | Tam ............................ 378/15 |
| 6,804,321 | B2 | * | 10/2004 | Katsevich ...................... 378/4 |
| 2002/0012417 | A1 | | 1/2002 | Bruder .......................... 378/4 |
| 2002/0015468 | A1 | | 2/2002 | Kohler .......................... 378/4 |
| 2002/0018540 | A1 | | 2/2002 | Stierstorfer .................. 378/16 |
| 2002/0021780 | A1 | | 2/2002 | Kohler ......................... 378/15 |
| 2002/0025018 | A1 | | 2/2002 | Takagi .......................... 378/8 |
| 2002/0037068 | A1 | | 3/2002 | Oikawa ........................ 378/15 |
| 2002/0050970 | A1 | | 5/2002 | Kajihara ....................... 345/89 |
| 2002/0057756 | A1 | | 5/2002 | Marume ........................ 378/4 |
| 2003/0081715 | A1 | * | 5/2003 | Tam ............................. 378/4 |
| 2004/0125910 | A1 | * | 7/2004 | Katsevich .................... 378/15 |

OTHER PUBLICATIONS

Kudo, et al., *Extended Bone–Beam Reconstruction Using Radom Transform*; IEEEE, 1997, p. 16931697.

Kachelrie, et al., *Advanced Single–Slice Rebinning in Cone–Beam Spiral CT*, Med. Phys. 27 (4), Apr. 2000, p 754–772.

Bruder, et al., *Single–Slice Rebinning Reconstruction in Spiral Cone–Beam Computer Tomography*, IEEE V. 19, No. 9 Sep. 2000, p. 873–887.

Schaller, et al., *Exact Radon Rebinning Algorithm for the Long Object Problem in Helical Cone–Beam CT*, IEEE, vol. 19 No. 5, May 2000, p. 361–375.

Turbell, et al., *Helical Cone–Beam Tomography*, 2000 John Wiley & Sons, Inc. p. 91–100.

Defrise, et al., *A Solution to the Long–Object Problem in Helical Cone–Beam Tomography*, Phys, Med. Biol.45 (2000) p. 623–643.

Noo et al., *Approximate Short–Scan Filtered–Backprojection for Helical CB Reconstruction*, IEEE 1999, p. 2073–2077.

Kudo, et al., *A New Approach to Exact Cone–Beam Reconstruction Without Radon Transfer*, IEEE, 1999 p. 1636–1643.

* cited by examiner

Fig. 4

Step 30. Finding two sets of lines for filtering

Step 31. Choose a discrete set of values of the parameter $s_2$ inside the interval $I$ that corresponds to the trajectory of the x-ray source $C$.

↓

Step 32. For each selected $s_2$ find the vector $\dot{y}(s_2)$, which is tangent to $C$ at $y(s_2)$.

↓

Step 33. For each selected $s_2$ find the line, which is obtained by intersecting the plane through $y(s_0)$, $y(s_2)$, and parallel to $\dot{y}(s_2)$, with the plane $DP(s_0)$.

↓

Step 34. The collection of lines constructed in Step 33 is the required first set of lines $L_1(s_2)$.

↓

Step 35. Let $\omega$ be the polar angle in the plane perpendicular to $\dot{y}(s_0)$ and $e(\omega)$ be the corresponding unit vector perpendicular to $\dot{y}(s_0)$.

↓

Step 36. For a discrete set of values $\omega$, find lines obtained by intersecting the plane through $y(s_0)$ and parallel to $\dot{y}(s_2)$, $e(\omega)$, with the plane $DP(s_0)$.

↓

Step 37. The collection of lines constructed in Step 36 is the required second set of lines $L_2(\omega)$.

↓

Step 40

METHOD OF RECONSTRUCTING IMAGES FOR SPIRAL AND NON-SPIRAL COMPUTER TOMOGRAPHY

This invention relates to computer tomography, and in particular to processes and systems for reconstructing three-dimensional images from the data obtained by spiral and non-spiral scans, and this invention is a Division of 10/389,090 filed Mar. 14, 2003 now U.S. Pat. No. 6,771,733, and is a continuation-in-part of U.S. application Ser. No. 10/143,160 filed May 10, 2002, now U.S. Pat. No. 6,574,299, entitled: Exact Filtered Back Projection (FBP) Algorithm For Spiral Computer Tomography, which claims the benefit of U.S. Provisional Application 60/312,827 filed Aug. 16, 2001, and this invention claims the benefit of priority to U.S. Provisional Application 60/379,547 filed May 10, 2002, all by the same inventor, and by the same assignee as the subject application, which are all incorporated by reference.

BACKGROUND AND PRIOR ART

Over the last thirty years, computer tomography (CT) has gone from image reconstruction based on scanning in a slice-by-slice process to spiral scanning. From the 1970s to 1980s the slice-by-slice scanning was used. In this mode the incremental motions of the patient on the table through the gantry and the gantry rotations were performed one after another. Since the patient was stationary during the gantry rotations, the trajectory of the x-ray source around the patient was circular. Pre-selected slices through the patient have been reconstructed using the data obtained by such circular scans. From the mid 1980s to present day, spiral type scanning has become the preferred process for data collection in CT. Under spiral scanning a table with the patient continuously moves through the gantry that is continuously rotating about the table. At first, spiral scanning has used one-dimensional detectors, which receive data in one dimension (a single row of detectors). Later, two-dimensional detectors, where multiple rows (two or more rows) of detectors sit next to one another, have been introduced. In CT there have been significant problems for image reconstruction especially for two-dimensional detectors. In what follows the data provided by the two-dimensional detectors will be referred to as cone-beam (CB) data or CB projections.

In addition to spiral scans there are non-spiral scans, in which the trajectory of the x-ray source is different from spiral. In medical imaging, non-spiral scans are performed using a C-arm device.

For three-dimensional (also known as volumetric) image reconstruction from the data provided by a spiral and non-spiral scans with two-dimensional detectors, there are two known groups of algorithms: Exact algorithms and Approximate algorithms, that each have known problems. Under ideal circumstances, exact algorithms can provide a replication of an exact image. Thus, one should expect that exact algorithms would produce images of good quality even under non-ideal (that is, realistic) circumstances. However, exact algorithms can be known to take many hours to provide an image reconstruction, and can take up great amounts of computer power when being used. These algorithms can require keeping considerable amounts of cone beam projections in memory. Additionally, some exact algorithms can require large detector arrays to be operable and can have limits on the size of the patient being scanned.

Approximate algorithms possess a filtered back projection (FBP) structure, so they can produce an image very efficiently and using less computing power than Exact algorithms. However, even under the ideal circumstances they produce an approximate image that may be similar to but still different from the exact image In particular, Approximate algorithms can create artifacts, which are false features in an image. Under certain circumstances these artifacts could be quite severe.

To date, there are no known algorithms that can combine the beneficial attributes of Exact and Approximate algorithms into a single algorithm that is capable of replicating an exact image under the ideal circumstances, uses small amounts of computer power, and reconstructs the exact images in an efficient manner (i.e., using the FBP structure). Here and everywhere below by the phrase that the algorithm of the invention reconstructs an exact image we will mean that in theory the algorithm is capable of reconstructing an exact image. Since in real life any data contains noise and other imperfections, no algorithm is capable of reconstructing an exact image.

Image reconstruction has been proposed in many U.S. Patents. See for example, U.S. Pat. Nos.: 5,663,995 and 5,706,325 and 5,784,481 and 6,014,419 to Hu; U.S. Pat. Nos. 5,881,123 and 5,926,521 and 6,130,930 and 6,233,303 to Tam; U.S. Pat. No. 5,960,055 to Samaresekera et al.; U.S. Pat. No. 5,995,580 to Schaller; U.S. Pat. No. 6,009,142 to Sauer; U.S. Pat. No. 6,072,851 to Sivers; U.S. Pat. Nos. 6,173,032 and 6,459,754 to Besson; U.S. Pat. No. 6,198,789 to Dafni; U.S. Pat. Nos. 6,215,841 and 6,266,388 to Hsieh. However, none of the patents overcome all of the deficiencies to image reconstruction referenced above.

SUMMARY OF THE INVENTION

A primary objective of the invention is to provide a general scheme for creating improved processes and systems for reconstructing images of objects that have been scanned in a spiral or non-spiral fashions with two-dimensional detectors.

In the general setting application of the invented scheme requires finding of a weight function, which would lead to the required inversion algorithm. As a particular case, we show how this general scheme applies to a C-arm scan with the closed x-ray source trajectory and gives us a new, theoretically exact and efficient (i.e., with the convolution-based FBP structure) reconstruction algorithm.

In this particular case we demonstrate how that weight function is found. In addition, we show that the algorithms disclosed in the parent patent Ser. No. 10/143,160 filed May 10, 2002, entitled: Exact Filtered Back Projection (FBP) Algorithm For Spiral Computer Tomography, which claims the benefit of U.S. Provisional Application 60/312,827 filed Aug. 16, 2001, all by the same inventor, and by the same assignee as the subject application, which are all incorporated by reference, also fit into the proposed general scheme by demonstrating the appropriate vectors and coefficients.

Further objects and advantages of this invention will be apparent from the following detailed description of the presently preferred embodiments.

BRIEF DESCRIPTION OF THE FIGURES

FIG. 4 is a seven substep flow chart for finding two sets of lines for filtering, corresponding to step 30 of FIG. 2.

DESCRIPTION OF THE PREFERRED EMBODIMENTS

Figure 1:
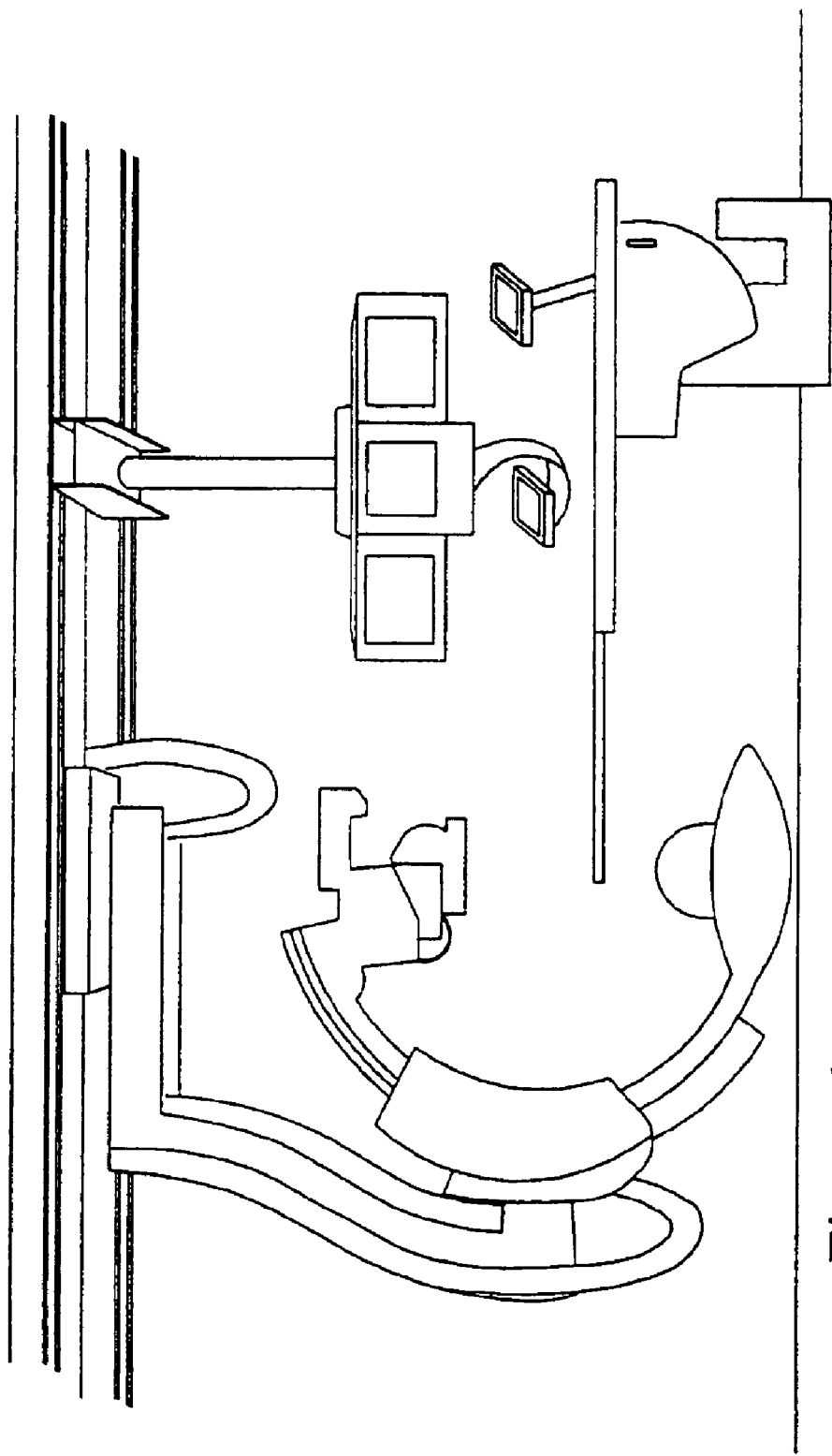
FIG. 1 shows a c-arm scan assembly that can be used with the subject invention.

Before explaining the disclosed embodiments of the present inventions in detail it is to be understood that the invention is not limited in its application to the details of the particular arrangements shown since the invention is capable of other embodiments. Also, the terminology used herein is for the purpose of description and not of limitation.

For purposes of clarity, several definitions of terms being used in this invention will now be described.

Beam can be defined as a beam of particles (such as x-ray particles) that experience for the most part non-scattering interactions as they pass along straight lines through the medium (such as patient) to be scanned. Thus, an individual particle emitted by a source either is absorbed by the medium or travels all the way through it unabsorbed.

Cone beam can be defined as any conical shaped beam (i.e. not necessarily with round cross-section).

The two-dimensional detector (or, detector) can be defined as any device on which the cone beam is incident and which is capable of measuring intensity of the beam as a two-dimensional function (e.g., at a two-dimensional array of points).

This invention is a continuation-in-part of U.S. application Ser. No. 10/143,160 filed May 10, 2002, entitled: Exact Filtered Back Projection (FBP) Algorithm For Spiral Computer Tomography, which claims the benefit of U.S. Provisional Application 60/312,827 filed Aug. 16, 2001, all by the same inventor, and by the same assignee as the subject application, which are all incorporated by reference.

The invention will now be described in more detail by first describing the main inversion formula followed by the novel algorithm. First we introduce the necessary notations. C is a smooth curve in $R^3$:

$$I \to R^3, I \ni s \to y(s) \in R^3, \tag{1}$$

Here $I \subset R$ is a finite union of intervals. $S^2$ is the unit sphere in $R^3$, and $$D_f(y, \Theta) := \int_0^\infty f(y + \Theta t) dt, \quad \Theta \in S^2; \tag{2}$$

$$\beta(s, x) := \frac{x - y(s)}{|x - y(s)|}, \quad x \in U, s \in I; \tag{3}$$

$$\Pi(x,\xi) := \{z \in R^3 : (z-x)\cdot\xi = 0\}. \tag{4}$$

Additionally, $f$ is the function representing the distribution of the x-ray attenuation coefficient inside the object being scanned, $D_f(y,\beta)$ is the cone beam transform of $f$, and $\beta(s,x)$ is the unit vector from the focal point $y(s)$ pointing towards the reconstruction point x. For $\beta \in S^2$, $\beta^\perp$ denotes the great circle $\{\alpha \in S^2 : \alpha \cdot \beta = 0\}$. Given $x \in R^3$ and $\xi \in R^3 \setminus 0$, let $s_j = s_j(\xi, \xi \cdot x)$, $j = 1, 2, \ldots$, denote points of intersection of the plane $\Pi(x,\xi)$ with C. Also $\dot{y}(s) := dy/ds;$
$\ddot{y}(s) := d^2y/ds^2.$ Given the focal point $y(s)$ (also referred to as source position), let DP(s) denote a plane where a virtual flat two-dimensional detector can be located for the purpose of measuring the cone-beam projection corresponding to the focal point $y(s)$.

Introduce the sets $$Crit(s, x) := \{\alpha \in \beta^\perp(s, x) : \Pi(x, \alpha) \text{ is tangent to} \tag{5}$$
$$C \text{ or } \Pi(x, \alpha) \text{ contains an endpoint of } C\}$$

$$I_{reg}(x) := \{s \in I : Crit(s, x) \text{ is a subset of but not}$$
$$\text{equal to } \beta^\perp(s, x)\} Crit(x) := \bigcup_{s \in I} Crit(s, x).$$

Sometimes Crit(s,x) coincides with $\beta^\perp(s,x)$. This happens, for example, if $\beta(s,x)$ is parallel to $\dot{y}(s)$ or the line through $y(s) \in C$ and x contains an endpoint of C. If $\alpha \in S^2 \setminus Crit(x)$ we say that such $\alpha$ is non-critical.

Fix any $x \in R^3 \setminus C$ where $f$ needs to be computed. The main assumptions about the trajectory C are the following.

Property C1. (Completeness condition) Any plane through x intersects C at least at one point.

Property C2. The number of directions in Crit(s,x) is uniformly bounded on $I_{reg}(x)$.

Property C3. The number of points in $\Pi(x,\alpha) \cap C$ is uniformly bounded on $S^2 \setminus Crit(x)$.

Property C1 is the most important from the practical point of view. Properties C2 and C3 merely state that the trajectory C is not too exotic (which rarely happens in practice).

An important ingredient in the construction of the inversion formula is weight function $n_0(s,x,\alpha), s \in I_{reg}(x), \alpha \in \beta^\perp(s,x) \setminus Crit(s,x)$. Define $$n_\Sigma(x, \alpha) = \sum_j n_0(s_j, x, \alpha), s_j = s_j(\alpha, \alpha \cdot x), \alpha \in S^2 \setminus Crit(x) \tag{6}$$

$$n(s, x, \alpha) = \frac{n_0(s, x, \alpha)}{n_\Sigma(x, \alpha)} \tag{7}$$

In equation (6) and everywhere below $\Sigma_j$ denotes the summation over all $s_j$ such that $y(s_j) \in C \cap \Pi(x,\alpha)$. The main assumptions about $n_0$ are the following.

Property W1. $n_\Sigma(x,\alpha) > 0$ on $S^2$.

Property W2. There exist finitely many continuously differentiable functions $\alpha_k(s,x) \in \beta^\perp(s,x), s \in I_{reg}(x)$, such that n(s, x,$\alpha$) is locally constant in a neighborhood of any (s,$\alpha$), where $s \in I_{reg}(x)$ and $$\alpha \in \beta^\perp(s, x), \quad \alpha \notin \left(\bigcup_k \alpha_k(s, x)\right) \cup Crit(s, x).$$

The inversion formula, which is to be derived here, holds pointwise. Therefore, if $f$ needs to be reconstructed for all x belonging to a set U, then properties C1–C3, W1, and W2, are supposed to hold pointwise, and not uniformly with respect to $x \in U$.

Let $\alpha_1(s)$ and $\alpha_2(s)$ be two smooth vector functions with the properties $\beta(s,x)\cdot\alpha_1(s)=\beta(s,x)\cdot\alpha_2(s)=\alpha_1(s)\cdot\alpha_2(s)=0, |\alpha_1(s)|=|\alpha_2(s)|=1.$ Then we can write $$\alpha=\alpha(s,\theta)=\alpha_1(s)\cos\theta+\alpha_2(s)\sin\theta. \tag{8}$$

Let $\alpha^\perp(s,\theta):=\beta(s,x)\times\alpha(s,\theta)$. The polar angle $\theta$ is introduced in such a way that $$\alpha^\perp(s,\theta) = \frac{\partial}{\partial\theta}\alpha(s,\theta).$$

Denote $$\phi(s,x,\theta):=sgn(\alpha\cdot\dot{y}(s))n(s,x,\alpha), \alpha=\alpha(s,\theta). \tag{9}$$

Then the general reconstruction formula is given by $$f(x) = -\frac{1}{8\pi^2}\sum_m \int_I \frac{c_m(s,x)}{|x-y(s)|} \times \tag{10}$$

$$\int_0^{2\pi} \frac{\partial}{\partial q} D_f(y(q), \cos\gamma\beta(s,x) +$$

$$\sin\gamma\alpha^\perp(s,\theta_m))\bigg|_{q=s} \frac{d\gamma}{\sin\gamma} ds.$$

Here $\theta_m$'s are the points where $\phi(s,x,\theta)$ is discontinuous; and $c_m(s,x)$ are values of the jumps:

$$c_m(s,x) := \lim_{\varepsilon\to 0^+}(\phi(s,x,\theta_m+\varepsilon)-\phi(s,x,\theta_m-\varepsilon)). \tag{11}$$

A brief step-by-step description of a general image reconstruction algorithm based on equations (10), (11) is as follows.

Figure 2:
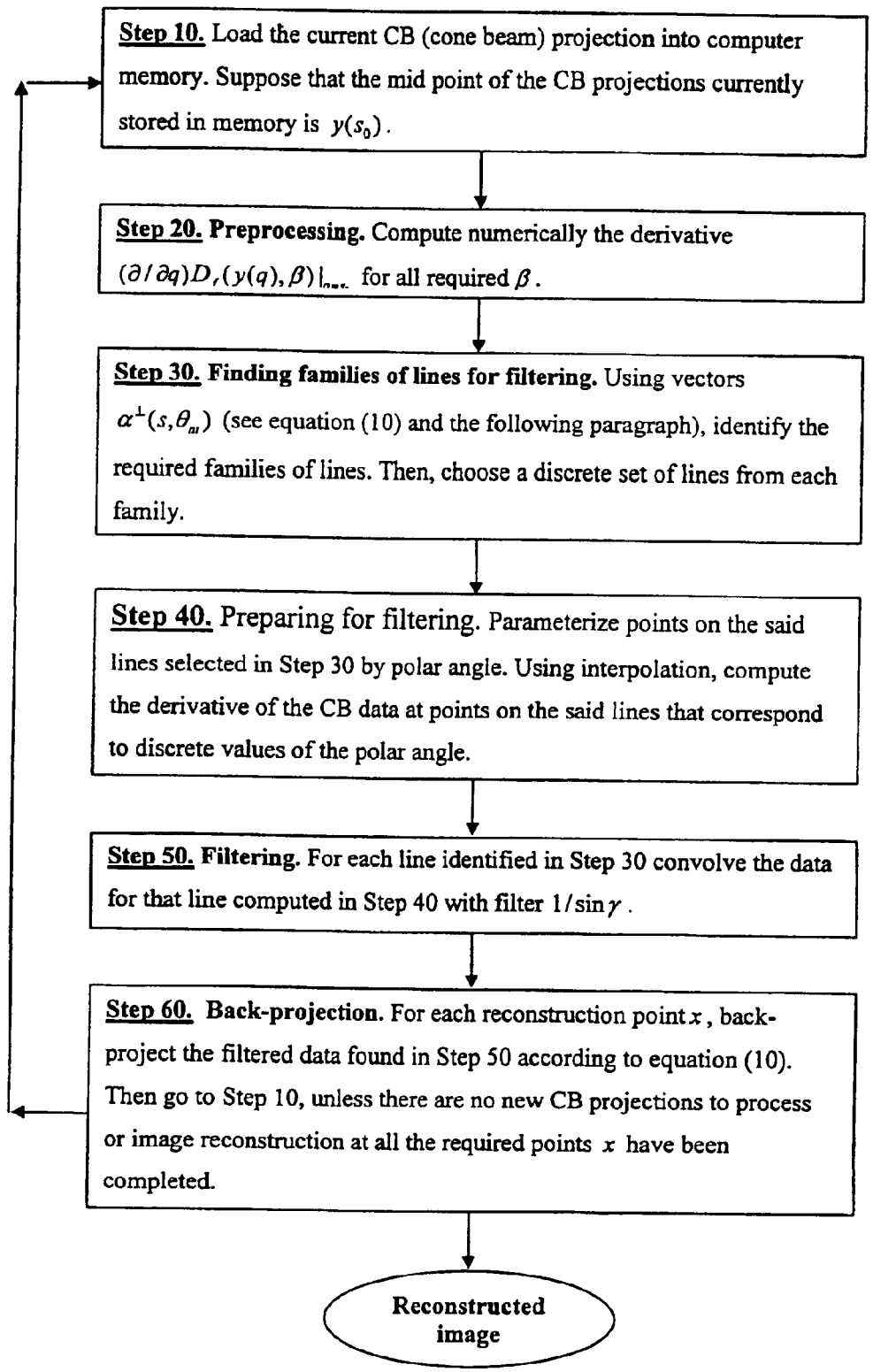
FIG. 2 shows an overview of the basic process steps of the invention.

FIG. 2 shows an overview of the basic process steps 10, 20, 30, 40, 50, 60 of the invention. The steps will now be described.

Step 10. Load the current CB (cone beam) projection into computer memory. Suppose that the mid point of the CB projections currently stored in memory is $y(s_0)$.

Step 20. Preprocessing. Compute numerically the derivative $(\partial/\partial q)D_f(y(q),\beta)|_{q=s_0}$ for all required $\beta$.

Step 30. Finding families of lines for filtering. Using vectors $\alpha^\perp(s,\theta_m)$ (see equation (10) and the following paragraph), identify the required families of lines. Then, choose a discrete set of lines from each family.

Step 40. Preparing for filtering. Parameterize points on the said lines selected in Step 30 by polar angle. Using interpolation compute the derivative of the CB data at points on the said lines that correspond to discrete values of the polar angle.

Step 50. Filtering. For each line identified in Step 30 convolve the data for that line computed in Step 40 with filter $1/\sin\gamma$.

Step 60. Back-projection. For each reconstruction point x back-project the filtered data found in Step 50 according to equation (10). Then go to Step 10, unless there are no new CB projections to process or image reconstruction at all the required points x have been completed.

PARTICULAR CASES OF THE GENERAL FORMULA

Consider a spiral path of the x-ray source $$y_1(s)=R\cos(s), y_2(s)=R\sin(s), y_3(s)=s(h/2\pi), h>0. \tag{12}$$

Here s is a real parameter;
h is pitch of the spiral;
R is distance from the x-ray source to the isocenter.

It is known in the literature that any point strictly inside the spiral belongs to one and only one PI segment (see P. E. Danielsson et al. "Towards exact reconstruction for helical cone-beam scanning of long objects. A new detector arrangement and a new completeness condition" in "Proc. 1997 Meeting on Fully 3D Image Reconstruction in Radiology and Nuclear Medicine (Pittsburgh)", eds. D. W. Townsend and P. E. Kinahan, yr. 1997, pp. 141–144, and M. Defrise, F. Noo, and H. Kudo "A solution to the long-object problem in helical cone-beam tomography", Physics in Medicine and Biology, volume 45, yr. 2000, pp. 623–643). Recall that a PI segment is a segment of line endpoints of which are located on the spiral and separated by less than one pitch in the axial direction. Let $s=s_b(x)$ and $s=s_t(x)$ denote values of the parameter corresponding to the endpoints of the PI segment containing x. We will call $I_{PI}(x):=[s_b(x), s_t(x)]$ the PI parametric interval. The part of the spiral corresponding to $I_{PI}(x)$ will be denoted $C_{PI}(x)$. As C, which appears in Section 1, we will take the segment $C_{PI}(x)$. It is clear that any plane through x intersects $C_{PI}(x)$ at least at one point. Also, inside the PI parametric interval there exists $\check{s}=\check{s}(x)$ such that the plane through $y(\check{s})$ and parallel to $\dot{y}(\check{s}), \ddot{y}(\check{s})$, contains x.

DERIVATION OF THE INVERSION FORMULAS (24), (25) of U.S. parent patent application Ser. No. 10/143,160 filed May 10, 2002, entitled: Exact Filtered Back Projection (FBP) Algorithm For Spiral Computer Tomography, which claims the benefit of U.S. Provisional Application 60/312,827 filed Aug. 16, 2001, all by the same inventor, and by the same assignee as the subject application, which are all incorporated by reference. Let us construct now functions $e_k(s,x)$. Denote $$e_1(s,x) := \frac{[\beta(s,x)\times\dot{y}(s)]\times\beta(s,x)}{|[\beta(s,x)\times\dot{y}(s)]\times\beta(s,x)|}. \tag{13}$$

By construction, $e_1(s,x)$ is a unit vector in the plane through $y(s)$ and spanned by $\beta(s,x), \dot{y}(s)$. Moreover, $e_1(s,x)\perp\beta(s,x)$. Given $y(s)$, $s\in(s_b(x), s_t(x))\backslash\check{s}(x)$, find $s_{tan}\in I_{PI}(x)$, $s_{tan}\ne s$, such that the plane through x, $y(s)$, and $y(s_{tan})$ is tangent to $C_{PI}(x)$ at $y(s_{tan})$. This is equivalent to solving $$[(x-y(s_{tan}))\times(x-y(s))]\cdot\dot{y}(s_{tan})=0, s_{tan}\ne s. \tag{14}$$

Existence and uniqueness of the solution $s_{tan}\in I_{PI}(x)$ to (14) is shown in A. Katsevich "Theoretically exact FBP-type inversion algorithm for Spiral CT", SIAM Journal on Applied Mathematics, Vol. 62, pp. 2012–2026 (2002). It is also shown there that $s_{tan}(s,x)$ is smooth with respect to s on $(s_b(x), s_t(x))\backslash\check{s}(x)$ and is made continuous on $[s_b(x), s_t(x)]$ by setting $$s_{tan}(s,x)=s_t(x) \text{ if } s=s_b(x),$$

$$s_{tan}(s,x)=\check{s}(x) \text{ if } s=\check{s}(x),$$

$$s_{tan}(s,x)=s_b(x) \text{ if } s=s_t(x), \tag{15}$$

Once $s_{tan}=s_{tan}(s,x)$ has been found, denote similarly to (13)

$$e_2(s,x) := \frac{[\beta(s,x)\times\Theta]\times\beta(s,x)}{|[\beta(s,x)\times\Theta]\times\beta(s,x)|}, \tag{16}$$

where $$\Theta=sgn(s-s_{tan}(s,x))\beta(s_{tan},x) \text{ if } s\in(s_b(x),s_t(x))\backslash\check{s}(x),$$

$$\Theta=\dot{y}(s_{tan}) \text{ if } s\in\{s_b(x),\check{s}(x),s_t(x)\}. \tag{17}$$

By construction, $e_2(s,x)$ is a unit vector in the plane through x, $y(s)$, and tangent to $C_{PI}(x)$ at $y(s_{tan})$. In addition, $e_2(s,x) \perp \beta(s,x)$. Using equation (17) and the inequalities $s_{tan}(s,x) > \check{s}(x)$ if $s < \check{s}(x)$, $s_{tan}(s,x) < \check{s}(x)$ if $s > \check{s}(x)$, we conclude that $e_2(s,x)$ is continuous and piecewise smooth with respect to s on $[s_b(x), s_1(x)]$.

Define $$n_0(s,x,\alpha) = sgn(\alpha \cdot \dot{y}(s))[sgn(\alpha \cdot e_1(s,x)) + sgn(\alpha \cdot e_2(s,x))]. \quad (18)$$

It has been proven in A. Katsevich "Theoretically exact FBP-type inversion algorithm for Spiral CT", SIAM Journal on Applied Mathematics, Vol. 62, pp. 2012–2026 (2002), that in this case $n_\Sigma(x,\alpha) = 2$ a.e. on $S^2$ for all $s \in I_{PI}(x)$. Substituting into equation (9) and using equation (7) we obtain $$\phi(s, x, \theta) = \frac{1}{2}[sgn(\alpha(s, \theta) \cdot e_1(s, x)) + sgn(\alpha(s, \theta) \cdot e_2(s, x))]. \quad (19)$$

Thus, $\phi$ is discontinuous when $\alpha(s,\theta)$ is perpendicular to either $e_1(s,x)$ (and, consequently, $\dot{y}(s)$) or $e_2(s,x)$. The integral with respect to $\gamma$ in equation (10) is odd when $\theta \to \theta + \pi$. Similarly, the values of the jump of $\phi$ at two points $\theta_{m_1}$ and $\theta_{m_2}$ separated by $\pi$ differ by a factor $-1$. So, by inserting an extra factor 2, this integral can be confined to an interval of length $\pi$. This implies that we can take $\alpha^{\perp}(s,\theta_m) = e_m(s,x)$, m=1,2, and equation (10) transforms into the inversion formulas (24), (25) of U.S. parent patent application Ser. No. 10/143,160 filed May 10, 2002, entitled: Exact Filtered Back Projection (FBP) Algorithm For Spiral Computer Tomography, which claims the benefit of U.S. Provisional Application 60/312,827 filed Aug. 16, 2001, all by the same inventor, and by the same assignee as the subject application, which are all incorporated by reference, (note that all jumps of $\phi$ have amplitude 1):

$$f = \frac{1}{2}(B_1 f + B_2 f), \quad (20)$$

where $$(B_k f)(x) := \quad (21)$$
$$-\frac{1}{2\pi^2} \int_{I_{PI}(x)} \frac{1}{|x - y(s)|} \times \int_0^{2\pi} \frac{\partial}{\partial q} D_f(y(q), \cos\gamma\beta(s, x) +$$
$$\sin\gamma e_k(s, x))\bigg|_{q=s} \frac{d\gamma}{\sin\gamma} ds, k = 1, 2.$$

DERIVATION OF THE EQUATION (10) of parent U.S. application Ser. No. 10/143,160 filed May 10, 2002, entitled: Exact Filtered Back Projection (FBP) Algorithm For Spiral Computer Tomography, which claims the benefit of U.S. Provisional Application 60/312,827 filed Aug. 16, 2001, all by the same inventor, and by the same assignee as the subject application, which are all incorporated by reference. Choose any $\psi \in C^\infty([0, 2\pi])$ with the properties $$\psi(0) = 0; \ 0 < \psi'(t) < 1, \ t \in [0, 2\pi]. \quad (22)$$

Suppose $s_0$, $s_1$, and $s_2$ are related by $$s_1 \psi(s_2 - s_0) + s_0 \text{ if } s_0 \leq s_2 < s_0 + 2\pi,$$
$$s_1 \psi(s_0 - s_2) + s_2 \text{ if } s_0 - 2\pi < s_2 < s_0. \quad (23)$$

Since $\psi(0) = 0$, $s_1 = s_1(s_0, s_2)$ is a continuous function of $s_0$ and $s_2$. Equations (22) and (23) imply $s_1 \neq s_2$ unless $s_0 = s_1 = s_2$. In order to avoid unnecessary complications, we will assume in what follows $$\psi'(0) = 0.5; \ \psi^{(2k+1)}(0) = 0, \ k \geq 1 \quad (24)$$

If (24) holds, then $s_1 = s_1(s_0, s_2)$ is a $C^\infty$ function of $s_0$ and $s_2$. Conditions (22) and (24) are very easy to satisfy. One can take, for example, $\psi(t) = t/2$, and this leads to $$s_1 = (s_0 + s_2)/2, \ s_0 - 2\pi < s_2 < s_0 + 2\pi.$$

Denote also $$u(s_0, s_2) = \frac{y(s_1 \times y(s_0)) \times (y(s_2) - y(s_0))}{|(y(s_1) - y(s_0)) \times (y(s_2) - y(s_0))|} sgn(s_2 - s_0), \text{ if } 0 < |s_2 - s_0| < 2\pi, \quad (25)$$

$$u(s_0, s_2) = \frac{\dot{y}(s_0) \times \ddot{y}(s_0)}{|(\dot{y}(s_0) \times \ddot{y}(s_0))|}, \text{ if } s_2 = s_0. \quad (26)$$

It is shown in A. Katsevich "Improved exact FBP algorithm for Spiral CT" submitted for possible publication to the journal "Advances in Applied Mathematics" in November 2001, that such $s_2$ exists, is unique, and depends smoothly on $s_0$. Therefore, this construction defines $s_2 := s_2(s_0, x)$ and, consequently, $u(s_0, x) := u(s_0, s_2(s_0, x))$. Finally, we set $$e(s,x) := \beta(s,x) \times u(s,x), \ n_0(s,x,\alpha) := sgn(\alpha \cdot \dot{y}(s)) sgn(\alpha \cdot e(s,x)). \quad (27)$$

It is proven in A. Katsevich "Improved exact FBP algorithm for Spiral CT" submitted for possible publication to the journal "Advances in Applied Mathematics" in November 2001, that in this case $n_\Sigma(x,\alpha) = 1$ on $S^2$ for all $s \in I_{PI}(x)$. Substitution into equation (9) and using equation (7) gives $$\phi(s,x,\theta) = sgn(\alpha(s,\theta) \cdot e(s,x)). \quad (28)$$

So $\phi$ is discontinuous when $\alpha(s,\theta)$ is perpendicular to $e(s,x)$. Arguing in the same way as before, we immediately obtain the inversion formula equation (10) of U.S. parent patent application Ser. No. 10/143,160 filed May 10, 2002, entitled: Exact Filtered Back Projection (FBP) Algorithm For Spiral Computer Tomography, which claims the benefit of U.S. Provisional Application 60/312,827 filed Aug. 16, 2001, all by the same inventor, and by the same assignee as the subject application, which are all incorporated by reference:

$$f(x) = -\frac{1}{2\pi^2} \int_{I_{PI}(x)} \frac{1}{|x - y(s)|} \times \int_0^{2\pi} \frac{\partial}{\partial q} \quad (29)$$
$$D_f(y(q), \cos\gamma\beta(s, x) + \sin\gamma e_k(s, x))\bigg|_{q=s} \frac{d\gamma}{\sin\gamma} ds.$$

How to Obtain New Inversion Formulas

Returning to the case of a general trajectory C, take $n_0(s,x,\alpha) = 1$. It follows from the completeness condition that $n_\Sigma(x,\alpha) \geq 1$ on $S^2$. So equation (10) becomes an inversion formula in which the constants $c_m$ can easily be determined before a scan knowing the trajectory of the x-ray source C. By construction, the inversion formula is theoretically exact. In the same way is in U.S. parent patent application Ser. No. 10/143,160 filed May 10, 2002, entitled: Exact Filtered Back Projection (FBP) Algorithm For Spiral Computer Tomography, which claims the benefit of U.S. Provisional Application 60/312,827 filed Aug. 16, 2001, all by the same inventor, and by the same assignee as the subject application, which are all incorporated by reference, one immediately sees that the formula admits convolution-based filtered back-projection implementation. The function $\phi(s, x, \theta)$ is discontinuous whenever the plane $\Pi(x,\alpha(s,\theta))$ is tangent to C or contains endpoints of C, or $\alpha(s,\theta) \perp e_k(s,x)$ for some k. This means that, in general, for every point x in a region of interest one would have to compute the contribution from the endpoints to the image. If the trajectory of the x-ray source is short (e.g., as in C-arm scanning), this should not cause any problems. However, for long trajectories (e.g., as is frequently the case in spiral scanning), this is undesirable. The approach developed in Section 1 allows one to construct formulas that would not require computing contributions from the endpoints. From equations (6)–(11) it follows that one has to find the function $n_0(s,x,\alpha)$ so that for all $s \in I_{reg}$ the function $\phi(s,x,\theta)$ is continuous when the plane $\Pi(x,\alpha(s,\theta))$ passes through an endpoint of C. Note that in the case of C-arm scanning if the trajectory C is closed, such a problem does not arise and we obtain an exact FBP-type inversion formula.

DETAILED DESCRIPTION OF THE NEW GENERAL INVERSION ALGORITHM

As an example we will illustrate how the algorithm works in the case when the trajectory C of a C-arm is closed and $n_0(s,x,\alpha) \equiv 1$. The algorithm will consist of the following steps 10, 20, 30, 40, 50 and 60 as depicted in FIGS. 2–7.

Step 10(FIG. 2). Load the current CB projection into computer memory. Suppose that the mid point of the CB projections currently stored in memory is $y(s_0)$.

Figure 3:
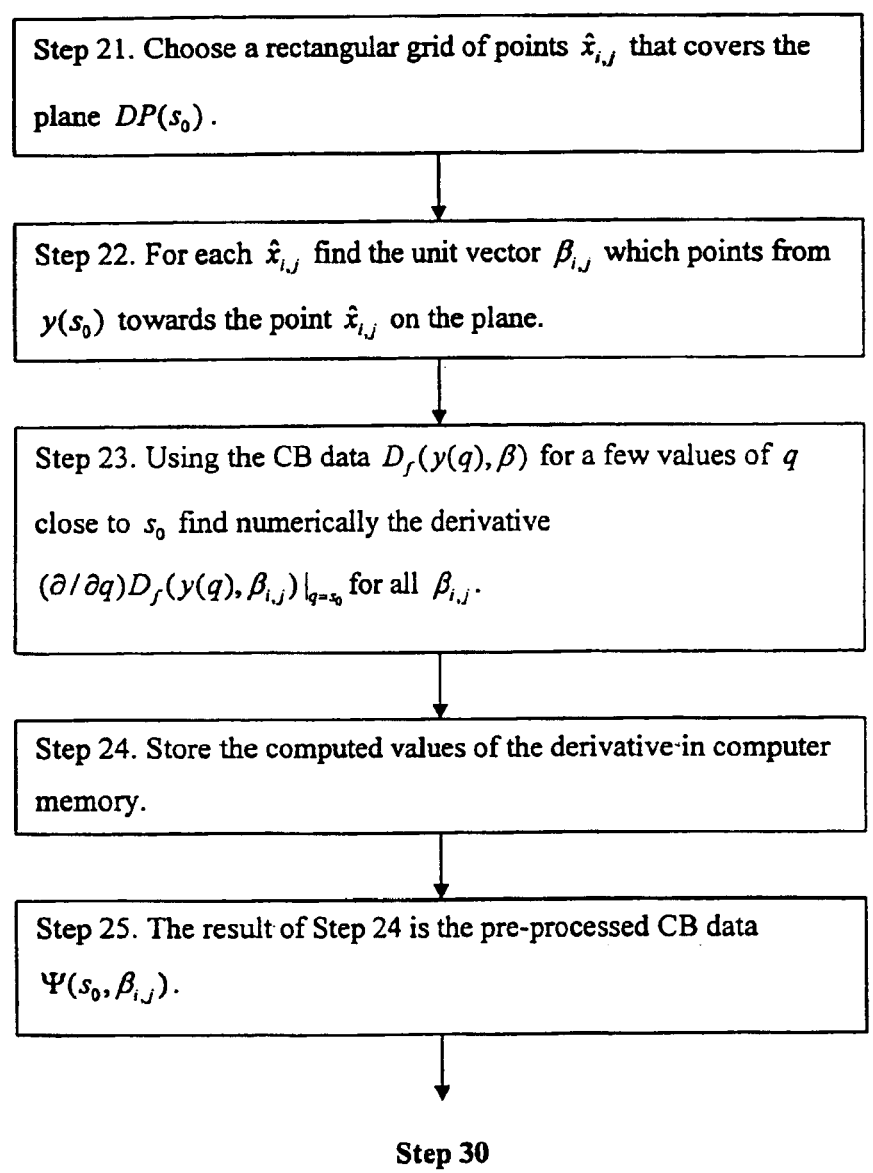
FIG. 3 is a five substep flow chart for preprocessing, corresponding to step 20 of FIG. 2.

Step 20(FIGS. 2–3). Preprocessing.

Step 21. Choose a rectangular grid of points $\hat{x}_{i,j}$ that covers the plane $DP(s_0)$.

Step 22. For each $\hat{x}_{i,j}$ find the unit vector $\beta_{i,j}$ which points from $y(s_0)$ towards the point $\hat{x}_{i,j}$ on the plane $DP(s_0)$.

Step 23. Using the CB data $D_f(y(q),\beta)$ for a few values of q close to $s_0$ find numerically the derivative $(\partial/\partial q)D_f(y(q), \beta_{i,j})|_{q=s_0}$ for all $\beta_{i,j}$.

Step 24. Store the computed values of the derivative in computer memory.

Step 25. The result of Step 24 is the pre-processed CB data $\Psi(s_0,\beta_{i,j})$.

Step 30(FIGS. 2, 4). Finding two sets of lines for filtering.

Step 31. Choose a discrete set of values of the parameter $s_2$ inside the interval I that corresponds to the trajectory of the x-ray source C.

Step 32. For each selected $s_2$ find the vector $\dot{y}(s_2)$, which is tangent to C at $y(s_2)$.

Step 33. For each selected $s_2$ find the line, which is obtained by intersecting the plane through $y(s_0)$, $y(s_2)$, and parallel to $\dot{y}(s_2)$, with the plane $DP(s_0)$.

Step 34. The collection of lines constructed in Step 33 is the required first set of lines $L_1(s_2)$.

Step 35. Let $\omega$ be the polar angle in the plane perpendicular to $\dot{y}(s_0)$ and $e(\omega)$ be the corresponding unit vector perpendicular to $\dot{y}(s_0)$.

Step 36. For a discrete set of values $\omega$, find lines obtained by intersecting the plane through $y(s_0)$ and parallel to $\dot{y}(s_2)$, $e(\omega)$, with the plane $DP(s_0)$.

Step 37. The collection of lines constructed in Step 36 is the required second set of lines $L_2(\omega)$.

Figure 5:
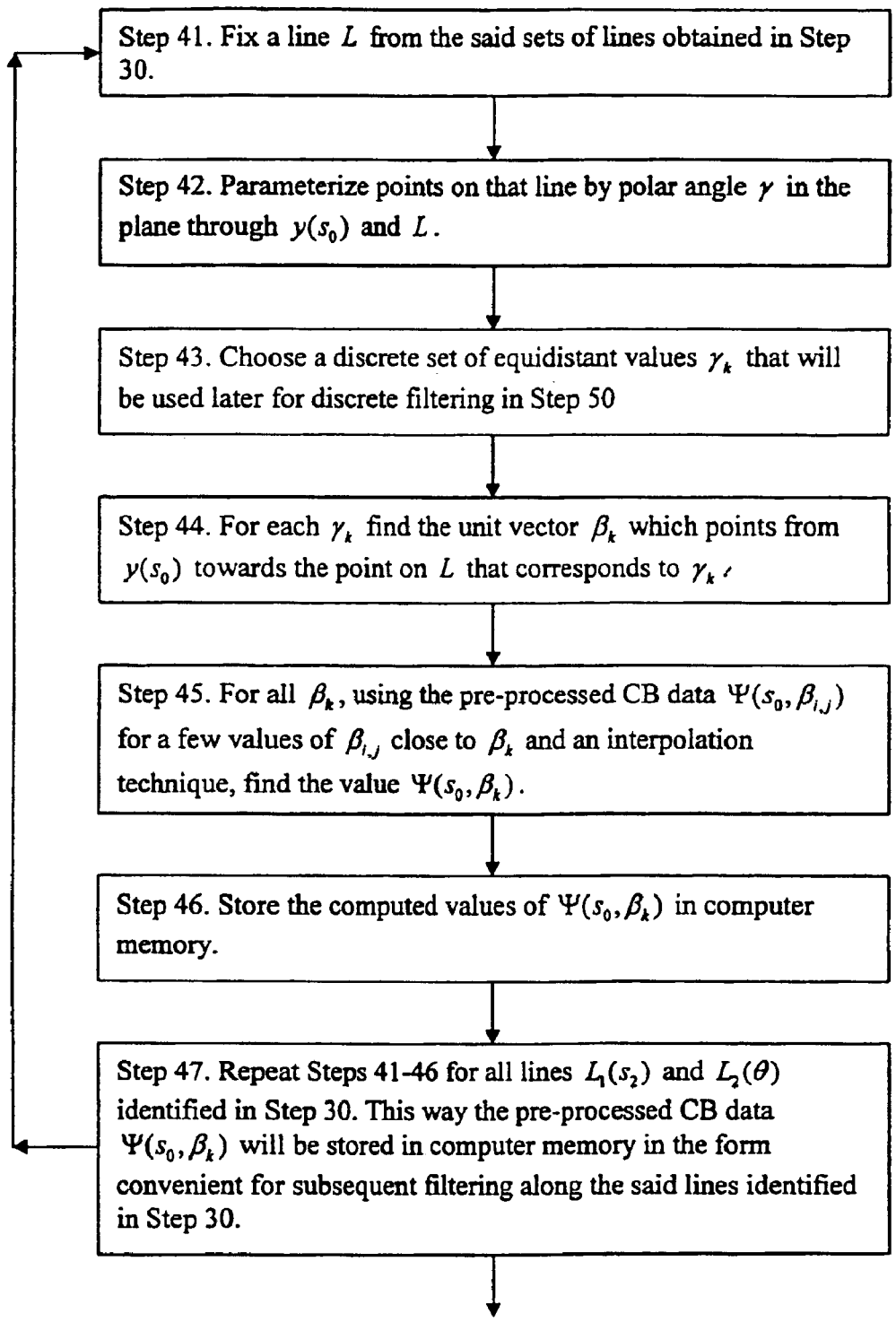
FIG. 5 is a seven substep flow chart for preparation for filtering, corresponding to step 40 of FIG. 2.

Step 40(FIGS. 2, 5). Preparation for filtering

Step 41. Fix a line L from the said sets of lines obtained in Step 30.

Step 42. Parameterize points on that line by polar angle $\gamma$ in the plane through $y(s_0)$ and L.

Step 43. Choose a discrete set of equidistant values $\gamma_k$ that will be used later for discrete filtering in Step 50.

Step 44. For each $\gamma_k$ find the unit vector $\beta_k$ which points from $y(s_0)$ towards the point on L that corresponds to $\gamma_k$.

Step 45. For all $\beta_k$, using the pre-processed CB data $\Psi(s_0,\beta_{i,j})$ for a few values of $\beta_{i,j}$ close to $\beta_k$ and an interpolation technique, find the value $\Psi(s_0,\beta_k)$.

Step 46. Store the computed values of $\Psi(s_0,\beta_k)$ in computer memory.

Step 47. Repeat Steps 41–45 for all lines $L_1(s_2)$ and $L_2(\theta)$ identified in Step 30.

This way the pre-processed CB data $\Psi(s_0,\beta_k)$ will be stored in computer memory in the form convenient for subsequent filtering along the said lines identified in Step 30.

Figure 6:
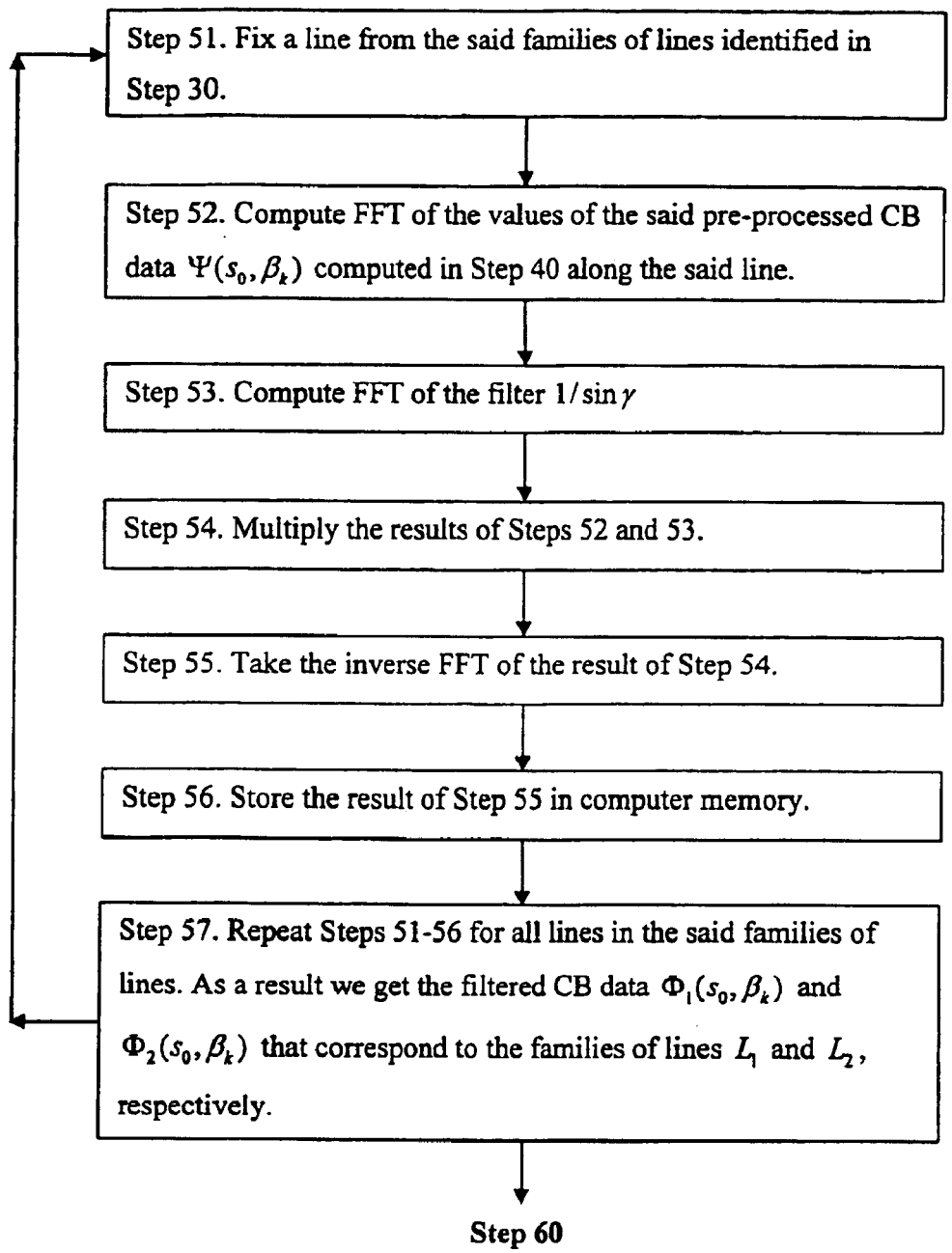
FIG. 6 is a seven substep flow chart for filtering, corresponding to step 50 of FIG. 2.

Step 50(FIGS. 2, 6). Filtering

Step 51. Fix a line from the said families of lines identified in Step 30.

Step 52. Compute FFT of the values of the said preprocessed CB data $\Psi(s_0,\beta_k)$ computed in Step 40 along the said line.

Step 53. Compute FFT of the filter $1/\sin\gamma$

Step 54. Multiply the results of Steps 52 and 53.

Step 55. Take the inverse FFT of the result of Step 54.

Step 56. Store the result of Step 55 in computer memory.

Step 57. Repeat Steps 51–56 for all lines in the said families of lines. As a result we get the filtered CB data $\Phi_1(s_0,\beta_k)$ and $\Phi_2(s_0,\beta_k)$ that correspond to the families of lines $L_1$ and $L_2$, respectively.

Figure 7:
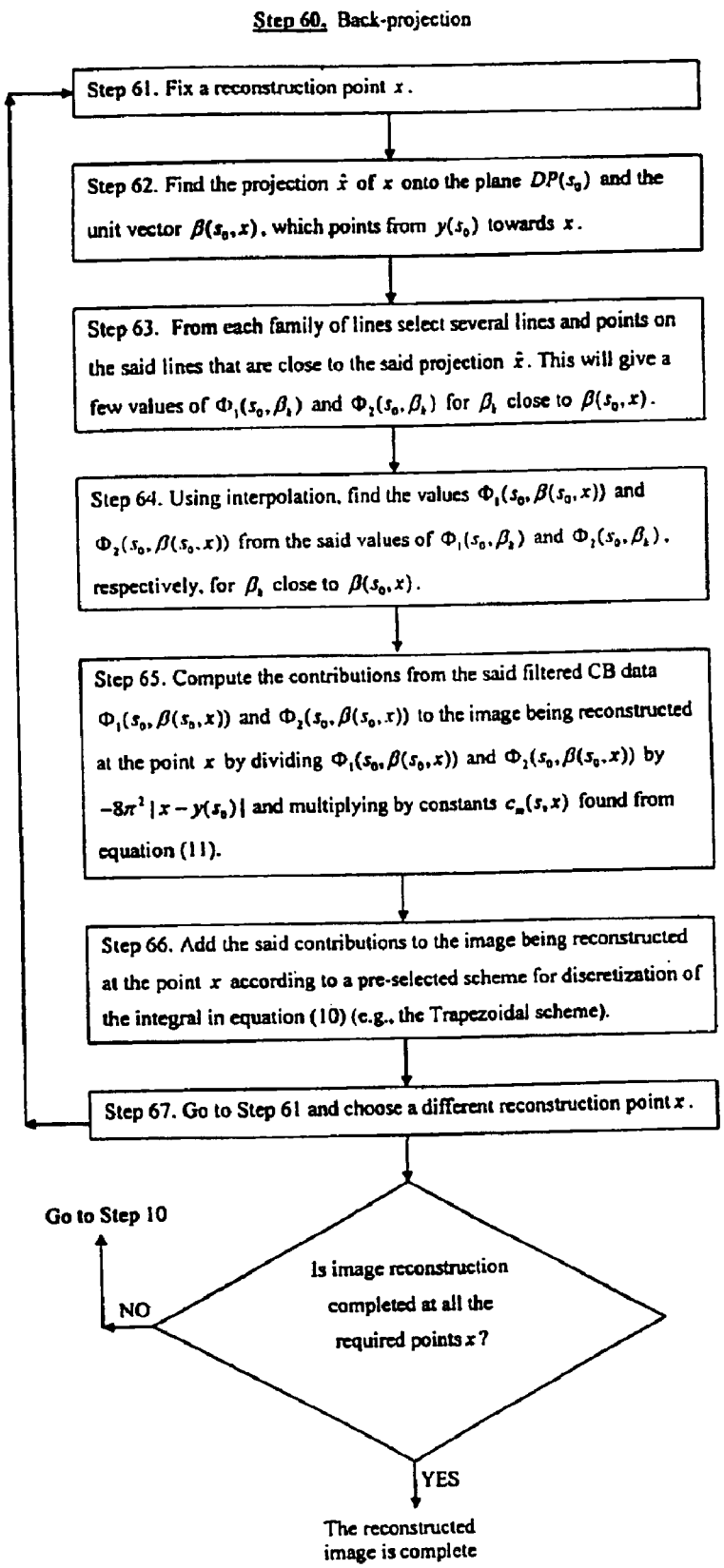
FIG. 7 is a seven substep flow chart for back-projection, corresponding to step 60 FIG. 2.

Step 60(FIGS. 2, 7). Back-projection

Step 61. Fix a reconstruction point x.

Step 62. Find the projection $\hat{x}$ of x onto the plane $DP(s_0)$ and the unit vector $\beta(s_0,x)$, which points from $y(s_0)$ towards x.

Step 63. From each family of lines select several lines and points on the said lines that are close to the said projection $\hat{x}$. This will give a few values of $\Phi_1(s_0,\beta_k)$ and $\Phi_2(s_0,\beta_k)$ for $\beta_k$ close to $\beta(s_0,x)$.

Step 64. Using interpolation, find the values $\Phi_1(s_0,\beta(s_0,x))$ and $\Phi_2(s_0,\beta(s_0,x))$ from the said values of $\Phi_1(s_0,\beta_k)$ and $\Phi_2(s_0,\beta_k)$, respectively, for $\beta_k$ close to $\beta(s_0,x)$.

Step 65. Compute the contributions from the said filtered CB data $\Phi_1(s_0,\beta(s_0,x))$ and $\Phi_2(s_0,\beta(s_0,x))$ to the image being reconstructed at the point x by dividing $\Phi_1(s_0,\beta(s_0,x))$ and $\Phi_2(s_0,\beta(s_0,x))$ by $|x-y(s_0)|$ and multiplying by constants $c_m(s,x)$ found from equation (11).

Step 66. Add the said contributions to the image being reconstructed at the point x according to a pre-selected scheme for discretization of the integral in equation (10) (e.g., the Trapezoidal scheme).

Step 67. Go to Step 61 and choose a different reconstruction point x.

Additional embodiments of the invented algorithm are possible. For example, if the two-dimensional detector is not large enough to capture the required cross-section of the cone-beam, one can assume that the missing data are zero or use an extrapolation technique to fill in the missing data, and then use the invented algorithm for image reconstruction. Since the missing data will be found approximately, the algorithm will no longer be able to provide the exact image.

The result will be an approximate image, whose closeness to the exact image will depend on how accurately the missing data are estimated.

Another embodiment arises when one integrates by parts with respect to s in equation (10) in the same way as in U.S. parent patent application Ser. No. 10/143,160 filed May 10, 2002, entitled: Exact Filtered Back Projection (FBP) Algorithm For Spiral Computer Tomography, which claims the benefit of U.S. Provisional Application 60/312,827 filed Aug. 16, 2001, all by the same inventor, and by the same assignee as the subject application, which are all incorporated by reference, to produce a version of the algorithm that requires keeping only one cone beam projection in memory at a time. An advantage of that version is that no derivative of the cone beam data along the trajectory of the radiation source is required.

More generally, one can come up with approximate algorithms that are based on the back-projection coefficients $c_m(s,x)$ and directions of filtering $a^{-1}(s,\theta_m)$, which are found from equations (9), (11). Such an approximate algorithm can either be based directly on equation (10) or the equation, which is obtained from it using integration by parts.

For the purpose of simplifying the presentation we used the notion of the plane $DP(s_0)$, which corresponds to a hypothetical virtual flat detector. In this case filtering is performed along lines on the plane. If the detector is not flat (e.g. it can be a section of the cylinder as is the case in spiral CT), then filtering will be performed not along lines, but along some curves on the detector array.

Although the invention describes specific weights and trajectories, the invention can be used with different weights for different or the same trajectories as needed.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method of computing images derived from computer tomography detectors, comprising the steps of:

(a) collecting cone beam data from a detector during a scan of an object;

(b) preprocessing the cone beam data, wherein the step of preprocessing includes (bi) computing the derivative of the said data along the source trajectory $$\frac{\partial}{\partial q} D_f(y(q),\Theta)\Big|_{q=s},$$

where
  $D_f$ is the cone beam data,
  q,s are variables along the source trajectory,
  y(q) is the source position as a function of q,
  $\Theta$ is a unit vector;

(c) identifying lines on a plane DP(s), where s is the parameter along the scan path and DP(s) is any plane intersecting the cone beam;

(e) convolving the said preprocessed data along said lines with filter $1/\sin(\gamma)$, where $\gamma$ is polar angle in the plane containing the current source position and a said line;

(f) back projecting said filtered data to form a precursor of said image; and (g) repeating steps a, b, c, d, e, and f until an image of the object is completed.

2. A method of computing images derived from computer tomography detectors, comprising the steps of:

(a) collecting cone beam data from a detector during a scan of an object;

(b) identifying lines on a plane $\Pi$ intersecting the cone beam, the said lines being filtering lines, (c) preprocessing said data along said filtering lines, wherein the step (c) of preprocessing includes computing the derivative of $D_f(y(s),\Theta)$ with respect to $\Theta$ along a direction non-parallel to the plane determined by y(s) and a filtering line, the said plane being a filtering plane, here
  s is parameter along the scan path, which determines point y(s) on the said path,
  $D_f(y,\Theta)$ is the cone beam transform of $f$ corresponding to the x-ray source located at the point y and the direction $\Theta$,
  $f$ is a function describing the object being scanned;

(d) shift invariant filtering said preprocessed data along said filtering lines, wherein the step (d) of filtering includes
  (i) convolving the data $D_f(y(s),\Theta)$ with kernel $1/\sin(\gamma)$ within a filtering plane, where $\gamma$ is polar angle in the plane,
  (ii) convolving the derivative of $D_f(y(s),\Theta)$ with a kernel $\cot(\gamma)$ within a filtering plane, the derivative of $D_f(y(s),\Theta)$ is the derivative with respect to $\Theta$ along a direction non-parallel to the filtering plane, (e) back projecting said filtered data to form a precursor of said image; and (f) repeating steps a, b, c, d, and e until an image of the object is reconstructed.

* * * * *

UNITED STATES PATENT AND TRADEMARK OFFICE
CERTIFICATE OF CORRECTION

PATENT NO. : 6,898,264 B2  
APPLICATION NO. : 10/858008  
DATED : May 24, 2005  
INVENTOR(S) : Alexander Katsevich Page 1 of 1

It is certified that error appears in the above-identified patent and that said Letters Patent is hereby corrected as shown below:

Col. 1, line 4 insert

-- STATEMENT REGARDING FEDERALLY SPONSORED RESEARCH OR DEVELOPMENT

This subject invention was made with government support under the National Science Foundation, federal contract numbers DMS9704285 and DMS0104033. The government has certain rights in this invention. --

Signed and Sealed this
First Day of March, 2011

David J. Kappos
*Director of the United States Patent and Trademark Office*